United States Patent
Nussbaum et al.

(10) Patent No.: US 6,331,402 B1
(45) Date of Patent: Dec. 18, 2001

(54) REDUCTION OF INTERFERENCE OF IMMUNOASSAYS BY SUBSTANCES DERIVED FROM THE FRAMEWORK REGIONS OF ANTIBODIES

(75) Inventors: Sabine Nussbaum, Iffeldorf; Ellen Moessner, Buehlerzell; Helmut Lenz, Tutzing; Gerald Praast, Schlangenbad, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/344,587

(22) Filed: Jun. 25, 1999

(30) Foreign Application Priority Data

Jun. 26, 1998 (DE) ............................................... 198 28 466

(51) Int. Cl.[7] .......................... C12Q 1/00; G01N 33/53; G01N 33/567; G01N 33/574; G01N 33/537
(52) U.S. Cl. ............................... 435/7.1; 435/4; 435/7.2; 435/7.21; 435/7.23; 435/7.92; 436/512; 530/300; 530/326; 530/329
(58) Field of Search ................... 436/512; 435/4, 435/7.1, 7.2, 7.21, 7.23, 7.92; 530/300, 326, 329

(56) References Cited

U.S. PATENT DOCUMENTS

| | | | |
|---|---|---|---|
| 4,861,711 | 8/1989 | Friesen et al. | 436/7 |
| 4,914,040 | 4/1990 | Lenz et al. | 436/175 |
| 5,614,367 | 3/1997 | Kaluza et al. | 435/7.1 |
| 5,804,371 | 9/1998 | Hoss et al. | 435/5 |
| 5,958,783 | 9/1999 | Josel et al. | 436/84 |

FOREIGN PATENT DOCUMENTS

| | | | |
|---|---|---|---|
| 1304683 | 7/1992 | (CA) | G01N/33/543 |
| 0 174 026 A2 | 3/1986 | (EP) | G01N/33/577 |
| WO 91/16627 | 10/1991 | (WO) | G01N/33/53 |

OTHER PUBLICATIONS

Turpelnen et al. Interference by Human Anti–Mouse Antibodies in CA 125 Assay after Immunoscintigraphy: Anti–Idiotypic Not Neutralized by Mouse IgG but Removed by Chromatography. Clin. Chem. 36(7):1333–1338, 1990.*

Koper et al. Quantitation of IgG and IgM Human Anti–Mouse Antibodies (HAMA) Interference in CA 125 Measurements Using Affinity Chromatography. Clin. Chem. Lab. Med. 36(1):23–8, 1998.*

Baum, R. P., "Clinical Course of Ovarian Cancer Patients Under Repeated Stimulation of HAMA Using MAb OC125 and B43.13," Hybridoma 12(5):583–589 (1993).

Boscato, Lynette M., et al., "Heterophilic Antibodies: a Problem for All Immunoassays," Clin. Chem. 34(1):27–33 (1988).

Buckel, Peter, et al., "Cloning and nucleotide sequence of heavy–and light–chain cDNAs from a creatine–kinase–specific monoclonal antobody," Gene 51:13–19 (1987).

Donnerstag, B., "Immunological profile of patients with ovarian cancer under immunostimulation with murine monoclonal antibodies," International Journal of Oncology 6:853–858 (1995).

Holz, Elena, "Monoclonal Antibodies in Cancer Therapy," Clin. Immunother. 5(3):214–222 (1996).

Juweid Malik, "Clinical Evaluation of Tumor Targeting with the Anticarcinoembryonic Antigen Murine Monoclonal Antibody Fragment, MN–14 F(ab)2," American Cancer Society 78(1):157–168 (1996).

Kanda, Hidetoshi, et al., "Construction and Expression of Chimeric Antibodies by a Simple Replacement of Heavy and Light Chain V Genes into a Single Cassette Vector," Hybridoma 13(5):359–366 (1994).

Kinders, Robert J., et al., "Interference in Immunoassays by Human Anti–mouse Antibodies," Eur. J. Cancer 26(5):647–648 (1990).

Kuroki, Masahide, et al., "Reducing interference from heterophilic antibodies in a two–site immunoassay for carcinoembryonic antigen (CEA) by using a human/mouse chimeric antibody to CEA as the tracer," Journal of Immunological Methods 180:81–91 (1995).

Livingston, Philip O., et al., "Impact of Immunological Adjuvants and Administration Route on HAMA Response after Immunization with Murine Monoclonal Antibody MELIMMUNE–1 in Melanoma Patients," Vaccine Research 4(2):87–94 (1995).

Nap, M., et al., "Immunohistochemical Characterization of 22 Monoclonal Antibodies against the CA125 Antigen: 2nd Report from the ISOBM TD–1 Workshop," Tumor Biol. 17:325–331 (1996).

Nustad, K., et al., "Specificity and Affinity of 26 Monoclonal Antibodies against the CA 125 Antigen: First Report from the ISOBM TD–1 Workshop," Tumor Biol. 17:196–219 (1996).

Rixon, Mark W., et al., "Preferential Use of a H Chain V Region in Antitumor–Associated Glycoprotein–72 Monoclonal Antibodies," The Journal of Immunology 151 (11):6559–6568 (1993).

Roitt, et al., "Chapter 7, Antigen Recognition," Immunology, pp. 7.1–7.10 (1989).

(List continued on next page.)

*Primary Examiner*—Sheela Huff
*Assistant Examiner*—Alana M. Harris
(74) *Attorney, Agent, or Firm*—Marilyn Amick; Roche Diagnostics Corporation

(57) ABSTRACT

The invention concerns an immunological process for the detection of an analyte in a sample, in particular of tumor markers wherein for the reduction of interference substances containing a peptide sequence derived from the framework regions of the variable domain of the antibodies to be detected or the antibodies used for immune therapy or scintigraphy are added to the test preparation. Furthermore, the invention concerns the use of such substances for the reduction of interference of immunoassays, a suppressive agent and a process for the reduction of interference of immunoassays by the substances mentioned.

6 Claims, 1 Drawing Sheet

OTHER PUBLICATIONS

White, C. A., et al., "Review of Single Agent IDEC–C2B8 Safety and Efficacy Results in Low–Grade or Follicular Non–Hodgkin's Lymphoma (NHL)," Europ. J. of Cancer 33(5):S40 (1997).

Xiang, Jianhua, et al., "Production of Murine V–Human Crl Chimeric Anti–Tag72 Antibody Using V Region cDNA Amplified by PCR," Molecular Immunology 27(8):809–817 (1990).

* cited by examiner

```
            1                   20         30                                               70                            100
OC125   -VQLQQSGPELVKPGASVKMSCKASGYIFT-DYYMKWVKQ--SHGREWIGDINLNNGDTFYNQKFKGRATLTVDKSSSTAYMQLNSLTSEDSAVYYCARSDDYGMDY------WGQGTTVTVSS
B72.3   QVQLQQSDAELVKPGASVKISCKASGYTFT-DHAIHWAKQKPEQGLEWIGYISPGNDDIKYNEKFKGKATLTADKSSTAYMQLNSLTSEDSAVYFCKRS-----YYG---HWGQGTTVTVSS
CD4     QVQHLQQSGPELVKPGPSVKMSCKASGYTFT-DYVVSWMQQRTGQVLEWIGEIYPGSGSAYYNEKFKGKAILTADKSSSTAYMEFSSLTSEDSAVFFCARRGDGSLGFA----HWGQGTLVTVAA
PSA-M66 QVQLQQSGAELVKPGASVKISCKATGYTFS-SYWIEWMKQRPGHGLEWIGDFLPGSGSSYFNEKFKGRATFTADSSNTAFMEFGSLTSEDSAVYYCARRGAGRVDY------WGQGTTLTVSA
MAK33   EVQGVESGGGLVKPGGSLKLSCAASGFTFS-DYYMYWVRQTPEKRLEWVATISDGGSYTYYPDSVKGRFTISRDNAKNNLYLQMSSLKSEDTAMYCARDKAYYGNYGDAMDYWGQGTSVTVSS
TSH A8  EVQLQESGPDLVKPSQSLSLTCTVTGYPITSGYTWHWIRQFP--CLEWMGYM-HYNGSTNYNPSLKSRISITRDTSKNQFFLQLNSVTTEDTATYYCEFSS--------WDYWGQGTSVTVSA
```

Figure 1

REDUCTION OF INTERFERENCE OF IMMUNOASSAYS BY SUBSTANCES DERIVED FROM THE FRAMEWORK REGIONS OF ANTIBODIES

The present invention concerns an immunological process for the detection of an analyte in a sample, in particular of tumor markers, wherein substances containing a peptide sequence derived from the framework regions of the variable domain of the antibodies to be detected or the antibodies used for immune therapy or scintigraphy is added to the test preparation. The invention also concerns the use of such substances for the reduction of interference of immunoassays, a suppressive agent and a process for the reduction of interference of immunoassays by the substances mentioned.

In the field of diagnostics especially immunological detection processes have become very important during the last years. By these processes analytes can be detected in biological samples. These analytes are for example medicinal drugs, hormones, proteins, infectious agents, microorganisms and antibodies directed against these analytes. In particular in the diagnostics of cancer diseases the tumor antigens or tumor markers like e.g. CEA (carcinoembryonic antigen), PSA (prostate specific antigen) or CA 125 are detected immunologically depending on the disease.

All immunological detection reactions include a specific binding reaction between the substance to be detected (analyte) and at least one specific binding partner which specifically reacts with the analyte or which specifically binds to it. The analyte and the specific binding partner form a specific binding pair which generally is a complex between an antigen and an antibody or an antibody fragment. More than one analyte or more than one binding partner can react with each other in each reaction.

There are different possibilities how to detect these specific binding reactions. In general one of the binding partners of the specific binding reaction is labeled. Usual labelings are chromogens, fluorophores, substances capable of chemi- or electrochemiluminescence, radioisotopes, haptens, enzyme labels or substances which can form another specific binding pair such as biotin/streptavidin.

An essential problem of immunoassays is related to the possible unspecific binding reactions and undesired interactions between the specific binding partners of the immunoassay and the sample components. Such interactions generally lead to an increase in the background signal and to a stronger signal variance and consequently to a reduced sensitivity and specificity of the corresponding test. Depending on the kind of interference provoked by unspecific interactions false positive or false negative test results can occur.

This is the case when interference factors occur in human sera and particularly interact with immunoglobulin reagents of an immunoassay frequently used as binding partners and may thus have an effect on the immunoassay. Especially in immunoassays with two monoclonal antibodies considerable measuring errors with serious consequences for the further treatment of a patient (Kinders and Hass (1990) Eur. J. Cancer 26 (5), 647–648; Boscato and Stuart (1988) Clin. Chem. 34 (1), 27–33) may occur.

A large number of these interference factors can be classified as HAMA (human anti-mouse antibodies) which are antibodies present in the sample to be tested and directed against the specific antibodies used as reagents. Often the name HAMA-interference is also used for antibody interferences which were not provoked by contact with mouse immunoglobulin or which were not strictly specific for mouse immunoglobulin. By this HAMA interference unspecific cross-linking of the antibody bound to the solid phase with the labeled antibody to be detected can for example occur in a conventional sandwich assay despite the absence of the analyte. As a consequence, a false positive signal results.

This problem has become bigger since recently immunoscintigraphy has been used more and more frequently in the diagnostics and therapy of tumors. For this purpose radioactively labeled monoclonal antibodies are injected in the bloodstream of the patient. Then the labeled antibodies specifically bind to the relevant tumor tissue. By subsequent scanning of the radioactivity, e.g. with a scintillation camera the tumor can be localized exactly. Immunologically stimulating therapies—even with monoclonal antibodies—are also used frequently to stimulate the formation of tumor-specific antibodies for the control of the tumor in the patient's organism.

When using these processes very high and partly very specific HAMA titers occur, as mentioned above, with increasing frequency in the patient sera (see for example Kath. et al. (1996) Oncology 2, 287–296; Holz et al. (1996) Clin. Immunther. 5 (3), 214–222; White et al. (1997) Europ. J. of Cancer 33(5), 40; Baum et al. (1993) Hybridoma 12(5), 583–589; Donnerstag et al. (1995) Int. J. Oncology 6, 853–858; Livingston et al. (1995) Vaccine Research 4 (2), 87–94; Jeweid et al. (1996) Cancer 78 (1), 157–168). They can also provoke interferences in tests involving chimeric antibodies. An important example of antibodies approved in the tumor therapy of colon carcinoma in Germany is the antibody 17-1A commercially named Panorex (Kath et al. (1996), supra; Holz et al. (1996), supra). In addition the list of the antibodies used in clinical studies includes a large number of further therapeutic reagents containing antibodies which very probably will be approved. Antibodies against CEA, CA125 and CA72.4 are already clinically applied in the immunological scintigraphy and it is expected that they will be used with increasing frequency too.

For state of the art elimination of these interference factors, often unspecific immunoglobulins or fragments thereof are used which are derived from the same strain of animal species as the antibodies used as reagents in the test. Thus alternative binding sites are offered to the interference factors where they can be taken up so that the specific immune reaction between the analyte and the antibodies is no more disturbed. For elimination of unspecific reactions in immunoassays using monoclonal mouse antibodies as reagents the addition of mouse or rat serum and, respectively, ascites is described in EP-A-0 174 026. A further possibility to avoid such interference is the addition of purified monoclonal Fab fragments or IgG molecules derived from the mouse which especially in a polymerized form develop a good suppressive effect according to U.S. Pat. No. 4,914,040.

To avoid false positive reactions for the detection of CEA the addition of a mixture of IgG molecules of different classes (IgGI, IgG2a, IgG2b) is recommended in the WO 91/16627. The provision of different immunoglobulin preparations in the quantities known and of a constant quality requires, however a lot of experimental time and mainly concerns the constant regions of the antibodies.

The reduction of the interference potential in the constant part of the antibody can also be achieved by the use of Fab fragments instead of intact immunoglobulins since the mainly occurring Fc interferences do not get a chance here due to the lacking Fc part. An optimized version are humanized antibodies with an Fv region composed of one mouse and one human part so that the susceptibility to interference can be further reduced even in the variable part (Kuroki et al. (1995) J. of Immunolog. Methods 180, 81–91). The use of chimeric antibodies with a variable mouse part and human constant regions can also reduce the susceptibility to interference of diagnostic tests.

According to the state of the art the addition of a protein and in particular of antibodies immunologically related to the antibodies used as detection reagents to avoid unspecifically increased or decreased values in the detection of an analyte is described too (EP-A-0 296 544). Due to the similarity of the antibodies added to the reagent antibodies used the substance interfering with these antibodies is captured selectively. For the provision of the suppressive antibodies it is recommended in the EP-A-0 296 544 to cleave off the antigen-binding structures of the reagent antibodies used, to block the antigen-binding structure by a complementary antigen structure, to change the antigen structure of the reagent antibody used by mutation or to use anti-idiotypical antibodies of the same subclass.

With the state of the art processes it is, however not possible to eliminate without much experimental input the interferences observed in the samples of patients previously treated with immunotherapeutic methods and which are very individual depending on the therapeutic antibody applied.

It was therefore an object to develop an improved process for the detection of an analyte and in particular tumor markers which would avoid any interference by unspecific substances such as HAMA to a large extent and better than with the state of the art. methods.

This object is achieved by a new immunological process for the detection of an analyte in a sample wherein for the reduction of interference substances are added to the test preparation containing a peptide sequence derived from the framework regions of the variable domain of the detection antibody or of the antibodies used for immunological therapy or scintigraphy.

In particular, substances are used containing sequence and/or structure characteristics occurring in the Fv regions of at least one of the specific detection antibodies used as a reagent in an immunoassay or which correspond to the sequences of a therapy/immunoscintigraphy which avoid any interference by HAMA almost completely. A particularly good suppressive effect can be observed when the substances used contain sequence or structure characteristics which occur in framework 1 or framework 3 of the heavy chain of the specific antibody/ies.

BRIEF DESCRIPTION OF THE DRAWINGS

For further explanation FIG. 1 lists the heavy chain sequences of the variable region of various antibodies one below the other. It becomes clear that in the framework region 1 (amino acid position 1 to 30) there is very much homology and to a large extent even identity among the tumor antibodies listed (OC125, B72.3, CD4 and PSA-M66). The same is true for the framework region 3 (amino acid position 69–100). The degree of homology in the heavy chain sequences of the variable region of the single tumor antibodies is here high too. A comparably low homology exists however between the sequences of the tumor antibodies and the respective sequences of the framework regions 1 and 3 of the non-tumor antibodies MAB33 and TSH antibody (TSH=thyroid stimulating hormone). The antibody B72.3 is described in xiang et al. 1990, Mol. Immunol. 27, p. 809–817 as well as in J. Immunology (1993), 151, 6559–6568; the antibody MAB33 is described in Buckel et al. 1987, Gene 51, 13–19; the antibody TSH-A8 in the EP-A-0 378 175; the antibody OC125 in Tumor Biology (1996), 17, 196–219 and 325–331 as well as in Hybridoma (1994) 13(5), 359–365).

According to the state of the art it has not been recognized that the immunological relationship of the antibodies is to be attributed to sequence homologies in the variable region of the antibody. Especially for HAMA interferences in patient samples showing very high and specific HAMA titers due to immunological scinitigraphy or immunologically stimulating therapies also by tumor-antigen directed mab the solution according to the invention is superior to that of the state of the art since these treatments with monoclonal antibodies lead to special, non-idiotypical but among themselves similar HAMA interferences in the samples to be tested particularly in different tumor marker tests.

The framework regions of an antibody are located in the variable part (Fv) of the molecule but do not really take part in antigen binding. They are essential for the characteristic folding of the variable part of the antibody and maintain the framework and structure of the antigen binding site (see for example Roitt et al. (1989) Immunology, Gower Medical Publishing, London, N.Y., chapter 7, Antigen Recognition).

For the process according to the invention antibodies are preferably used as the suppressive substance. The use of antibodies and their fragments has been proven to be particularly appropriate; their amino acid sequence of the framework region corresponds to the sequence of the detection antibodies used as reagents or the antibodies needed for therapy or immunological scintigraphy.

The monoclonal antibodies B72.3 (J. Immunology (1993), 151, 6559–6568) and OC125 (Tumor Biology (1996), 17, 196–219 and 325–331; Hybridoma (1994) 13 (5), 359–365) are used particularly preferably for the reduction of interference (see also the ISOBM report: Tumor Biology 1996; 17:196–219). Antibodies showing structure characteristics or binding properties equivalent to those of the antibodies B72.3 and OC125 can also be used for the reduction of interference.

For the suppressive effect of the antibodies used the amino acid sequence and the folding structure in the framework region 1 or 3 are essential. It should correspond to the sequences listed in FIG. 1 or should at least be very homologous to it. The homology is sufficient when a suppressive effect can be observed while using a suppressive antibody. In principle all antibodies having—in the framework regions 1 and/or 3 — one of the amino acid sequences listed in SEQ ID NO 1 to 8 are suitable for reduction of interference. The origin and the production of the antibodies used for the reduction of interference can be chosen at will. The monoclonal antibodies can be derived from ascites material or produced in the bioreactor according to methods known to the expert. The suppressive antibodies can but do not have to be derived from the same organism as the detection antibodies.

According to the invention HAMA interferences can be considerably reduced especially in processes for the detection of tumor markers. The reduction of interference of different tumor marker tests by the suppressive agent according to the invention is therefore surprising since tumor antigens are quite different in their amino acid sequences and structure. Surprisingly, it is however possible to suppress interferences in different tumor marker tests with one sequence-homologous reagent. One subject matter of the invention is therefore an immunological process for the detection of a tumor marker with reduction of interference by adding to the test preparation at least one substance—preferably antibodies—containing a peptide sequence derived from the framework regions of the variable domain of the antibodies to be detected or the antibodies used for immune therapy or scintigraphy.

The detection of the tumor markers CA125, CA15-3, CA19-9, CEA, PSA (in a free and complexed form) and AFP belong to the tests suppressed preferably. According to the invention processes for the detection of analytes not associated to tumor diseases, such as cardiovascular markers (like troponin T or myoglobin) are however very well suppressed too.

The term antibody means polyclonal or monoclonal antibodies. It also means the whole antibody as well as all fragments thereof usually applied in immunoassays and other uses, such as F(ab)'$_2$ Fab' or Fab fragments. The antibodies are produced according to methods known to the expert and can also be antibodies produced for example by genetic engineering. It is important that all substances used for reduction of interference contain one peptide sequence derived from the framework regions of the variable domain Fv of the detection antibodies.

The term detection antibody refers to immunoglobulins and their conjugates which are used as detection reagents in the test. In the case of a conventional sandwich assay the antibody bound to the solid phase and specifically binding to the analyte as well as the detection antibody specifically binding to the analyte on the one hand and carrying a label on the other hand belong to the detection antibodies. If further antibodies are necessary for the label detection (for instance in the case of the digoxigenin label which is detected with an enzyme labeled anti-digoxigenin antibody) they are also referred to as detection antibodies.

According to the invention one or several fragments of the framework regions—especially of the framework regions 1 and 3 of the Fv domain of the heavy immunoglobulin chain—can also be used as suppressive substances. These fragments are preferably peptides which can be synthesized by enzymatic digestion of the intact antibodies or by chemical reactions according to methods known to the expert.

Peptides containing peptide sequences from the framework regions 1 and 3 of the MAB OC125, B72.3, PSA or CD4 are suitable as substances used for the reduction of interference of immunological processes.

```
From the framework region 1:

QVQLQQSGPEASVKMSCKASGYIFT    (SEQ ID NO 1
                              from MAB OC125)

QVQLQQSDAEASVKISCKASGYTFT    (SEQ ID NO 2
                              from MAB B72.3)

QVQLQQSGAEASVKISCKATGYTFS    (SEQ ID NO 3
                              from MAB <PSA>M66)

QVHLQQSGPEPSVKMSCKASGYTFT    (SEQ ID NO 4
                              from MAB <CD4>)

From the framework-region 3:

RATLTVDKSSSTAYMQLNSLT        (SEQ ID NO 5
                              from MAB OC125)

KATLTADKSSSTAYMQLNSLT        (SEQ ID NO 6
                              from MAB B72.3)
```

```
RATFTADSSSNTAFMEFGSLT        (SEQ ID NO 7
                              from MAB<PSA>M66)

KAILTADKSSSTAYMEFSSLT        (SEQ ID NO 8
                              from MAB<CD4>)
```

Partial sequences of the peptides mentioned before with a length of at least 6 amino acids are also appropriate for the reduction of interference. The peptide sequences do not have to be present in an isolated form. They can also be flanked by further amino acid sequences which are not derived from the variable part of the antibody. It is also possible that the peptides are flanked by carbohydrate or lipid residues. A modification condition is however that the suppressive effect is maintained and that the modifications themselves do not provoke interferences within the immunoassay.

It is also conceivable that the peptides used for reduction of interference carry the corresponding sequence even several times, i.e. in a multimer form, and can thus also be used as polyhaptens. This means that for the production of a polyhapten the peptides according to the invention are coupled several times to one carrier. Different peptides according to the invention can be coupled to one carrier too. A macromolecule which does not take part in the immunological reaction itself, e.g. a bigger protein such as bovine serum albumin, latex particles, polystyrene, gold or dextran can serve as a carrier. The production of polyhaptens can be analogous to the method described in WO 96/03652.

The advantage of the substances for reduction of interference according to the invention is that for the removal of HAMA interferences a time- and cost intensive pretreatment of the samples such as PEG precipitation, protein A/G chromatography or heat treatment can be omitted.

According to the invention the test procedures and test formats can—in principle—be chosen arbitrarily. Homogeneous and heterogeneous procedures known to the expert are conceivable. The test formats preferred are heterogeneous formats with one specific binding partner coupled directly or indirectly to a solid phase. The conventional antigen detection in a sandwich format which is preferably used in tumor marker tests is mentioned here as an example. In the sandwich format the analyte (in our case an antigen) is bound like a sandwich between an antibody bound to a solid phase and a labeled antibody. The labeling is detected in one of the phases after the separation of the solid phase from the liquid phase.

Another example of the heterogeneous test procedure is the indirect detection of an analyte antibody via its binding to a solid-phase bound antigen. Here, the antibody is detected by a further labeled antibody's binding to the analyte antibody.

A further test format which can be suppressed according to the invention is the competitive test procedure with one solid-phase bound complex formed by two binding partners or antibodies specific for each other where the binding partner not directly bound to the solid phase is labeled. The analyte which depending on the test requirements is an antigen or an antibody displaces the labeled binding partner depending on its concentration from the complex. After separating the solid phase from the liquid phase the label is detected in one of the phases. Also in this case the suppressive substances according to the invention block the unspecific binding of interfering sample substances to the binding partners/antibodies used as detection reagents and thus avoid false test results as far as possible.

The maximum concentrations of the antibodies in the sample preparation used for reduction of interference are only given by the solubility of the antibodies in aqueous medium. Minimum concentrations of approximately 10 μg/ml to 40 μg/ml and upper limits of approximately 2 mg/ml, preferably 250 μg/ml antibody have proven to be appropriate.

Besides the substances according to the invention further suppressive measures can be taken if this is required. One of these measures is for instance the addition of MAB33 (Boehringer Mannheim GmbH, Germany, Ident. No. 1200 941) or of other antibodies with the same effect, poly MAB 33 (polymer mouse IgG, Boehringer Mannheim GmbH, Germany, Ident. No. 1368 338), RSA, salts, detergents.

Besides the so-called wet tests with test reagents in a liquid phase all other usual dry test formats appropriate for immunological detection of analytes can be used. In these dry tests or test strips as they are for example described in EP-A-9 186 799 the test components are applied on one carrier. In this case the suppressive agent according to the invention is applied to the dry test strip before the immunological reaction.

Preferably, the suppressive agent according to the invention should be added to the sample before or simultaneously with the binding partners used as detection reagents to enable as early as possible a reaction of the interfering unspecific substances with the suppressive agent.

All usual biological liquids known to the expert can be used as samples for the procedure of the immunoassays to be suppressed according to the invention. The substances preferred as samples are body liquids such as whole blood, blood serum, blood plasma, urine or saliva.

A further subject matter of the invention is a suppressive agent containing at least one substance including a peptide sequence derived from the framework regions of the variable domain of the antibodies to be detected or the antibodies used for immune therapy or scintigraphy. Further components of the suppressive agent can be buffers, salts and detergents known to the expert. The suppressive reagent can be provided in a liquid, aqueous or in a lyophilized form.

A further subject matter of the invention is a process for reduction of interference of immunoassays wherein especially for the suppression of HAMA effects substances containing a peptide sequence derived from the framework regions of the variable domain of the antibodies to be detected or the antibodies used for immune therapy or scintigraphy are added to the test preparation.

The invention is further described by the following examples.

EXAMPLE 1

Reduction of Interference of the CA125 Test with Different Suppressive Reagents

The CA 125 detection is performed according to the procedure described in the package leaflet of the Enzymun-Test® CA 125 II of Boehringer Mannheim GmbH, Germany (ident. No. 1 289 004). The test principle is a 1-step-sandwich ELISA based on the streptavidine technology. Two monoclonal CA125-specific antibodies specifically recognizing different epitopes on the CA125 are used. One of the antibodies is labeled with biotin and the other antibody with peroxidase. Together with an incubation solution containing biotinylated anti-CA125 antibodies and anti-CA125 antibodies labeled with peroxidase (POD) the sample is filled into a plastic tube coated with streptavidine. During the incubation the biotinylated antibody binds to the solid phase. The CA125 present in the sample binds to the biotinylated antibody. The antibody labeled with POD binds to the CA125 which is bound to the biotinylated antibody.

The sandwich complexes bound to the solid phase are detected by an indicator reaction after a washing step. For this, a substrate-chromogen solution containing ABTS® (2,2'-azino-di-[3-ethyl-benzthiazoline-sulfonic acid (6)]-diammonium salt) and $H_2O_2$ is added to the preparation. By the enzymatic activity of the peroxidase and depending on the amount of bound POD-labeled antibody a dye is built which can be detected photometrically.

Together with the biotinylated antibody 40 μg/ml of different suppressive state of the art reagents and—for comparison reasons—the suppressive reagent according to the invention are added to the test preparations.

The following substances are used as suppressive reagents: the solution according to the invention on the basis of the example MAB B72.3 (intact IgG), a HAMA suppressive reagent of the company Trina (mouse IgG), a HAMA suppressive reagent of the company Scantibodies (HBR, monoclonal anti-human IgM), the suppressive reagent MAB33 of Boehringer Mannheim GmbH, Germany (ident. No. 1 200 941), the suppressive reagent pMAB33 of Boehringer Mannheim GmbH, Germany (ident. No. 1 096 478) as well as three tumor marker antibodies against PSA, AFP and CEA.

Serum samples of patients with an ovary carcinoma having undergone an immune scintigraphy as well as commercially available HAMA panels and one normal serum (NS) of a healthy patient are used as samples. Table 1 shows the measuring values of the CA125 test with different suppressive reagents added. One POD unit (I U) corresponds to the enymatic activity oxidizing 1 μmol ABTS in one minute at 25° C. and a pH of 5.

TABLE 1

| | Values measured with the CA125 test | | | | | | | | |
|---|---|---|---|---|---|---|---|---|---|
| | CA125 Without addition U/ml | CA125 + B72.3 U/ml | CA125 + Trina-13 U/ml | CA125 + HBR U/ml | CA125 + MAB33 U/ml | CA125 + pMAB33 U/ml | CA125 + <PSA>-M66 U/ml | CA125 + <AFT>MTu11 U/ml | CA125 + <CEA>MTu3 U/ml |
| Normal serum | 16.42 | 23.4 | 20.64 | 15.48 | 14.62 | 15.12 | 9.25 | 12.5 | 7.16 |
| Immune scintigraphy with B43.13 (Ovary carcinoma) | >496 | 107.4 | 124.68 | 143.05 | 434.29 | 433.36 | 221.04 | 350.42 | 369.78 |

TABLE 1-continued

| | Values measured with the CA125 test | | | | | | | | |
|---|---|---|---|---|---|---|---|---|---|
| | CA125 Without addition U/ml | CA125 + B72.3 U/ml | CA125 + Trina-13 U/ml | CA125 + HBR U/ml | CA125 + MAB33 U/ml | CA125 + pMAB33 U/ml | CA125 + <PSA>–M66 U/ml | CA125 + <AFT>MTu11 U/ml | CA125 + <CEA>MTu3 U/ml |
| Immune scintigraphy with B43.13 (Ovary carzinoma) | 129 | 118.6 | 117.54 | 117.13 | 134.43 | 126.6 | 125.8 | 141.98 | 130.1 |
| Immune scintigraphy with B43.13 (Ovary carcinoma) | 262 | 96.5 | 106.65 | 117.31 | 158.04 | 160.89 | 111.9 | 157.97 | 158.63 |
| Commercially available HAMA-Panel III (Bioclinical Partners) | 111.7 | — | 34.42 | 35.3 | 50.77 | 55.65 | — | — | — |
| Immune scintigraphy with OC125 (Ovary carcinoma) | >496 | 289.7 | 329.93 | 322.77 | 348.52 | 360.41 | 300.2 | 402.03 | 335.33 |
| Commercially available HAMA-Panel (Starrate D) | 382.2 | 22.2 | 115.05 | 137.75 | 95.6 | 111.84 | 114.6 | 129.03 | 120.02 |
| Immune scintigraphy with B43.13 (Ovary carcinoma) | >496 | 158 | 404.09 | 420.97 | >496 | >496 | — | — | — |

Without suppressive reagents the CA125 test indicates positive measuring values which are however false positive values. It can be shown that with the monoclonal antibody B72.3 the best HAMA suppression. i.e. the lowest measuring value can be achieved. The suppressive agent according to the invention is thus clearly better than those of the state of the art. Among the tumor marker antibodies the PSA antibody has proven to be the most appropriate one for reduction of interference what is analogous to the sequence homology.

EXAMPLE 2

Reduction of Interference of the CA125 Test with <CD4>M3–10. MAB33 and the Panorex Antibody The detection of CA125 is performed according to example 1. For comparison the suppressive reagent according to the invention (here: MAB B72.3). polymerized and non-polymerized MAB33 as in example 1. the antibody <CD4>M3–10 and the Panorex antibody are used as suppressive reagents. The suppressive reagents are added in a concentration of 40 µg/ml.

TABLE 2

| | Values measured with the CA125 test | | | | | | | | | | |
|---|---|---|---|---|---|---|---|---|---|---|---|
| | CA125 without addition U/ml | CA125 + B72.3 U/ml | R % | CA125 + Panorex U/ml | R % | CA125 + <CD4> U/ml | R % | CA125 + PMAB33 U/ml | R % | CA125 + MAB33 U/ml | R % |
| TMC1 | 43.05 | 42.88 | 99 | 44.73 | 104 | 38.98 | 90 | 47.97 | 111 | 40.41 | 94 |
| TMC2 | 88.68 | 90.13 | 102 | 94.37 | 106 | 85.45 | 96 | 92.77 | 105 | 87.53 | 99 |
| Normal serum | 21.13 | 19.43 | 92 | 21.99 | 104 | 15.22 | 72 | 23.19 | 110 | 21.89 | 104 |
| Commercially available HAMA-Panel I (Bioclinical Partners) | 60.83 | 39.47 | 65 | 50.8 | 84 | 40.41 | 66 | 48.3 | 80 | 42.58 | 70 |
| Immune scintigraphy with B43.13 (Ovary carcinoma) | 142.94 | 77.44 | 54 | 93.98 | 66 | 77.61 | 54 | 89.87 | 63 | 77.82 | 54 |
| Commercially available HAMA-Panel (StarrateD) | 408.08 | 38.62 | 9 | 57.06 | 14 | 42.63 | 10 | 57.16 | 14 | 67.83 | 17 |
| Conmmercially available HAMA-Panel II (Bioclinical Partners) | >519 | 69.2 | <13 | 513.82 | <99 | 77.78 | <15 | 111.72 | <21 | 147.35 | 28 |

TABLE 2-continued

Values measured with the CA125 test

|  | CA125 without addition U/ml | CA125 + B72.3 U/ml | R % | CA125 + Panorex U/ml | R % | CA125 + <CD4> U/ml | R % | CA125 + PMAB33 U/ml | R % | CA125 + MAB33 U/ml | R % |
|---|---|---|---|---|---|---|---|---|---|---|---|
| Immune scintigraphy with OC125 (Ovary carcinoma) | >519 | 358.66 | <70 | 1350.1 | — | 465.88 | 90 | >519 | — | 1189.08 | — |
| Immune scintigraphy with B43.13 (Ovary carcinoma) | 239.26 | 39.64 | 17 | 119.11 | 50 | 45.84 | 19 | 103.22 | 43 | 112.67 | 47 |
| Immune scintigraphy with B43.13 (Ovary carcinoma) | 211.88 | 43.73 | 21 | 71.92 | 34 | 62.07 | 29 | 83.91 | 40 | 108.34 | 51 |

%R: percentage of recovery amount received in relation to the test without addition of suppressive reagent
TMC1 and TMC2: Tumor marker control of Boehringer Mannheim GmbH, Germany (ident.-No. 1 489 666), control serum on the basis of human serum with two required values, containing among others AFP, CEA, PSA, free PSA, CA125

It is shown that with the sequence homologous <CD4> antibody the suppression achieved is comparable to that of the antibody B72.3 but that the less sequence homologous Panorex antibody has a considerably lower suppressive effect (only a small signal decrease). In addition, the considerably lower effect of the state of the art suppressive reagents becomes evident.

EXAMPLE 3

Reduction of Interference of the CEA Test with Different Suppressive Reagents

To get a second criterion of the suppressive effect besides the CA125 test the CEA-Enzymun® test of Boehringer Mannheim GmbH (ident. No. 1448021) was chosen as matrix. The process is performed according to the procedure described in the package leaflet. Like in the CA125 test the test principle is also a 1-step-sandwich ELISA based on the biotin-streptavidine technology. Two monoclonal CEA-specific antibodies recognizing different epitopes on the CEA are used. One of the antibodies is labeled with biotin and the other antibody with peroxidase. Together with an incubation solution containing biotinylated anti-CEA antibodies and anti-CEA antibodies labeled with peroxidase (POD) the sample is filled into a plastic tube coated with streptavidine. During the incubation the biotinylated antibody binds to the solid phase. The CEA present in the sample binds to the biotinylated antibody. The antibody labeled with POD binds to the CEA which is bound to the biotinylated antibody.

The detection of the sandwich complexes bound to the solid phase is performed via the indicator reaction as described in the examples 1 and 2.

Reagents mentioned in the examples 1 and 2 as well as the OC125 antibody are used as suppressive reagents. They are added in a concentration of 10 µg/ml.

TABLE 3

Values measured with the CEA test

|  | CEA Enzymun ng/ml | CEA Enzymun + OC125 ng/ml | CEA Enzymun + B72-3 ng/ml | CEA Enzymun + HBR ng/ml | CEA Enzymun + MAB33 ng/ml |
|---|---|---|---|---|---|
| Normal serum | 0.79 | 1.01 | — | 1 | 1.1 |
| Immune scintigraphy with B43.13 (Ovary carcinoma) | 6.8 | 2.25 | 2.78 | 2.77 | 5.3 |
| Immune scintigraphy with B43.13 (Ovary carcinoma) | 7.84 | 3.01 | 3.62 | 3.4 | 6.09 |
| Commercially available HAMA-Panel III (Bioclinical Partners) | >51.6 | 4.98 | 6.89 | 9.1 | 17.72 |
| Immune scintigraphy with B43.13 (Ovary carcinoma) | 13.7 | 3.9 | — | 5.32 | 8.14 |
| Commercially avaiable HAMA-Panel (Starrate D) | 5.77 | 2.94 | 2.8 | 2.1 | 3.95 |
| Commercially available HAMA-Panel II (Bioclinical Partners) | 12.97 | 4.2 | 3.62 | 4.42 | 5.36 |
| Immune scintigraphy with <CEA> (Colon carcinoma) | 48.62 | 10.45 | 8.28 | 8.67 | 19.8 |

The results obtained with the suppressive reagents according to the invention MAB B72.3 and OC125 are to a certain extent comparable. Except a few amino acids these two antibodies are sequence homologous in the framework regions 1 and 3. The state of the art results of the suppressive effect are clearly worse.

EXAMPLE 4

Reduction of Interference of Different Test Systems

For comparison different tumor marker tests are shown that on the one hand are based on the Enzymun® test procedure (s. examples 1 to 3) and on the other hand on the Elecsys® procedure of Boehringer Mannheim GmbH. The Elecsys® procedure for all detections is based on the 1-step-sandwich principle with two antibodies recognizing different epitopes on the analytes (tumor markes) analogously to example 3. The solid phase is formed of magnetic latex beads coated with streptavidine to which binds a biotinylated antibody specific for the tumor marker. The bound tumor marker is detected after the separation of the solid phase from the liquid phase by measuring the electrochemiluminescence resulting from a second tumor-marker specific antibody labeled with a ruthenium complex.

Here, the suppressive effect of the solution according to the invention was tested with different Enzymun® and Elecsys®-tests:

CEA-Enzymun® (Ident.-No. 1448021; CEA Elecsys® (Ident.-No. 1731629); CA125 Enzymun® (Ident.-No. 1289004). CA125 Elecsys® (Ident.-No. 1776223); AFP Elecsys® (Ident.-No. 1731327); PSA tot. Enzymun® (Ident.-No. 1555332); PSA tot. Elecsys® (Ident.-No. 1731262); PSA free Enzymun® (Ident.-No. 1776444); PSA free Elecsys® (Ident.-No. 1820800).

The suppressive reagent MAB B72.3 is added in a concentration of 40 µg/ml.

The samples are high-titer HAMA sera from immune therapy or scintigraphy.

With CA125 both tests show a considerable reduction of the HAMA interference by addition of B72.3.

The interfering potential is also decreased with AFP. PSA total and free. With free PSA the interference susceptibility of the Elecsys® test is however higher than that of the Enzymun® test. A suppressive effect can thus be shown regardless of the test system.

EXAMPLE 5

Reduction of Interference in the Troponin-T and Myoglobin Tests

To show the suppressive effect also with other parameters than tumor markers the cardiovascular markers troponin T (Ident. No. 1 731 3 51) and myoglobin (Ident. No. 1 820 788) are chosen.

The test principle is based on the Elecsys® test described in example 4. Two monoclonal antibodies against troponin T and, respectively, myoglobin recognizing different epitopes on the analyte (troponin T and myoglobin) are used. One of the mab is labeled with biotin the other with a ruthenium complex the electrochemiluminescence signal of which is measured.

100 µg/ml of the suppressive reagent MAB B 72.3 are added to the test preparations.

TABLE 4

Reduction of interference of different test systems

| | CA125 Enz. | CA125 Enz. + B72.3 | CA125 ECL | CA125 ECL + B72.3 | AFP ECL | AFP ECL + B72.3 | PSA total Enz. | PSA total Enz. + B72.3 | PSA tot. ECL | PSA tot. ECL + B72.3 | PSA free Enz. | PSA free Enz. + B72.3 | PSA free ECL | PSA free ECL + B72.3 |
|---|---|---|---|---|---|---|---|---|---|---|---|---|---|---|
| Serum 1 | 339.1 | 24.9 | 21.6 | — | 16.98 | 12 | 1.62 | 0.2 | 0.73 | 0.2 | 0.35 | 0.12 | 0.73 | 0.15 |
| Serum 2 | >496 | 52.7 | 72.71 | 46.6 | 6.36 | 2.81 | 0.48 | 0 | 1.21 | 0.36 | 1.04 | 0.28 | 2.6 | 0.21 |
| Serum 3 | >496 | 370.2 | 186.6 | 133.1 | 4.73 | 1.87 | 0.75 | 0 | 1.12 | 0.17 | 1.62 | 0.32 | 4.93 | 0.27 |
| Serum 4 | >496 | 82.3 | 59.6 | 30.1 | 16.07 | 5.9 | 1.3 | 0.13 | 1.7 | 0.52 | 2.84 | 0.39 | 13.1 | 0.44 |
| Serum 5 | 205.8 | 23.01 | 24.3 | 2.33 | 1.85 | 0.07 | 0 | 0.27 | 0.05 | 0.11 | 0.03 | 2.23 | 0.12 | |
| Serum 6 | 181.1 | 28.65 | 29.62 | 2.03 | 1.52 | 0.07 | 0 | 0.38 | 0.1 | 0.25 | 0.08 | 3.57 | 0.24 | |
| Serum 7 | — | — | — | 2 | 1.24 | 0.14 | 0 | 0.41 | 0.14 | 0.45 | 0.18 | 2.7 | 0.34 | |

Enz. = Enzymun ®
ECL = Elecsys ®

TABLE 5

| | Myoglobin (ng/ml) | Myoglobin + 100 μg/ml B72.3 (ng/ml) | R % | Troponin T (ng/ml) | Troponin T + 100 μg/ml B72.3 (ng/ml) | R % |
|---|---|---|---|---|---|---|
| Control 1 | 99.229 | 100.396 | 101 | 0.148 | 0.148 | 100 |
| Control 2 | 1312.549 | 1283.688 | 98 | 7.261 | 7.325 | 101 |
| Immune therapy with B43.13 (Ovary carcinoma) | 19.819 | 14.888 | 75 | 0.015 | 0.011 | 73 |
| Commercially available HAMA-Panel (Starrate D) | 334.348 | 60.72 | 18 | 0.119 | 0.073 | 61 |
| Commercially available HAMA-Panet (Bioclinical Partners) | 210.342 | 42.318 | 20 | 0.187 | 0.121 | 65 |
| Immune therapy with OC125 (Ovary carcinoma) | 231.522 | 46.914 | 20 | 0.178 | 0.106 | 60 |
| Immune scintigraphy - <CEA>- MABs | 56.877 | 21.099 | 37 | 0.056 | 0.026 | 46 |
| Immune therapy with B43.13 (Ovary carcinoma) | 31.062 | 19.405 | 62 | 0.061 | 0.031 | 51 |

Reduction of interference of tests for the detection of troponin T and myoglobin Here too, the addition of B72.3 leads to remarkably lower signals and cancels the false positive measurement. The application of the suppressive reagents according to the invention is therefore also shown for markers other than tumor markers.

What is claimed is:

1. A method for the detection of an analyte in a biological sample suspected of containing said analyte and an interfering substance, said method comprising the steps of:
   a. forming a test mixture comprising
      i) said sample,
      ii) a binding partner specific for said analyte, and
      iii) an interference reducing substance in a concentration of at least about 10 μg/ml of the test mixture, said substance comprising a peptide sequence derived from framework region 1 or 3 of the variable domain of an antibody selected from the group consisting of said binding partner and antibodies used for immunological therapy or scintigraphy, wherein said interference reducing substance is not mouse serum and wherein said test mixture allows for binding of said analyte to said binding partner, and
   b. detecting said analyte present in said sample by measuring the binding between said analyte and said binding partner.

2. The method of claim 1 wherein said analyte is a tumor marker.

3. The method of claim 1 wherein said interference reducing substance is an antibody or antibody fragment.

4. The method of claim 1 wherein said peptide sequence is selected from the group consisting of SEQ ID Nos. 1–8 and partial sequences thereof, said sequence having a length of at least 6 amino acids.

5. The method of claim 1, wherein said analyte is CA125.

6. The method of claim 1 wherein said antibody is selected from the group consisting of B72.3, and OC125.

* * * * *

SEQUENCE LISTING

<160> NUMBER OF SEQ ID NOS: 14

<210> SEQ ID NO 1
<211> LENGTH: 25
<212> TYPE: PRT
<213> ORGANISM: Mus musculus

<400> SEQUENCE: 1

Gln Val Gln Leu Gln Gln Ser Gly Pro Glu Ala Ser Val Lys Met Ser
 1               5                  10                  15

Cys Lys Ala Ser Gly Tyr Ile Phe Thr
            20                  25

<210> SEQ ID NO 2
<211> LENGTH: 25
<212> TYPE: PRT
<213> ORGANISM: Mus musculus

<400> SEQUENCE: 2

Gln Val Gln Leu Gln Gln Ser Asp Ala Glu Ala Ser Val Lys Ile Ser
 1               5                  10                  15

Cys Lys Ala Ser Gly Tyr Thr Phe Thr
            20                  25

<210> SEQ ID NO 3
<211> LENGTH: 25
<212> TYPE: PRT
<213> ORGANISM: Mus musculus

<400> SEQUENCE: 3

Gln Val Gln Leu Gln Gln Ser Gly Ala Glu Ala Ser Val Lys Ile Ser
 1               5                  10                  15

Cys Lys Ala Thr Gly Tyr Thr Phe Ser

<210> SEQ ID NO 4
<211> LENGTH: 25
<212> TYPE: PRT
<213> ORGANISM: Mus musculus

<400> SEQUENCE: 4

Gln Val His Leu Gln Gln Ser Gly Pro Glu Pro Ser Val Lys Met Ser
 1               5                  10                  15

Cys Lys Ala Ser Gly Tyr Thr Phe Thr
            20                  25

<210> SEQ ID NO 5
<211> LENGTH: 21
<212> TYPE: PRT
<213> ORGANISM: Mus musculus

<400> SEQUENCE: 5

Arg Ala Thr Leu Thr Val Asp Lys Ser Ser Thr Ala Tyr Met Gln
 1               5                  10                  15

Leu Asn Ser Leu Thr
            20

<210> SEQ ID NO 6
<211> LENGTH: 21
<212> TYPE: PRT
<213> ORGANISM: Mus musculus

<400> SEQUENCE: 6

Lys Ala Thr Leu Thr Ala Asp Lys Ser Ser Thr Ala Tyr Met Gln
 1               5                  10                  15

Leu Asn Ser Leu Thr
            20

<210> SEQ ID NO 7
<211> LENGTH: 21
<212> TYPE: PRT
<213> ORGANISM: Mus musculus

<400> SEQUENCE: 7

Arg Ala Thr Phe Thr Ala Asp Ser Ser Ser Asn Thr Ala Phe Met Glu
 1               5                  10                  15

Phe Gly Ser Leu Thr
            20

<210> SEQ ID NO 8
<211> LENGTH: 21
<212> TYPE: PRT
<213> ORGANISM: Mus musculus

<400> SEQUENCE: 8

Lys Ala Ile Leu Thr Ala Asp Lys Ser Ser Thr Ala Tyr Met Glu
 1               5                  10                  15

Phe Ser Ser Leu Thr
            20

<210> SEQ ID NO 9
<211> LENGTH: 114
<212> TYPE: PRT
<213> ORGANISM: Mus musculus

<400> SEQUENCE: 9

Val Gln Leu Gln Gln Ser Gly Pro Glu Leu Val Lys Pro Gly Ala Ser
1               5                   10                  15

Val Lys Met Ser Cys Lys Ala Ser Gly Tyr Ile Phe Thr Asp Tyr Tyr
            20                  25                  30

Met Lys Trp Val Lys Gln Ser His Gly Arg Glu Trp Ile Gly Asp Ile
            35                  40                  45

Asn Leu Asn Asn Gly Asp Thr Phe Tyr Asn Gln Lys Phe Lys Gly Arg
        50                  55                  60

Ala Thr Leu Thr Val Asp Lys Ser Ser Thr Ala Tyr Met Gln Leu
65                  70                  75                  80

Asn Ser Leu Thr Ser Glu Asp Ser Ala Val Tyr Tyr Cys Ala Arg Ser
                85                  90                  95

Asp Asp Tyr Gly Met Asp Tyr Trp Gly Gln Gly Thr Thr Val Thr Val
                100                 105                 110

Ser Ser

<210> SEQ ID NO 10
<211> LENGTH: 114
<212> TYPE: PRT
<213> ORGANISM: Mus musculus

<400> SEQUENCE: 10

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Ala Lys Gln Lys Pro Glu Gln Gly Leu Glu Trp Ile
            35                  40                  45

Gly Tyr Ile Ser Pro Gly Asn Asp Asp Ile Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Val Thr Val
                100                 105                 110

Ser Ser

<210> SEQ ID NO 11
<211> LENGTH: 119
<212> TYPE: PRT
<213> ORGANISM: Mus musculus

<400> SEQUENCE: 11

Gln Val His Leu Gln Gln Ser Gly Pro Glu Leu Val Lys Pro Gly Pro
1               5                   10                  15

Ser Val Lys Met Ser Cys Lys Ala Ser Gly Tyr Thr Phe Thr Asp Tyr
            20                  25                  30

Val Val Ser Trp Met Gln Gln Arg Thr Gly Gln Val Leu Glu Trp Ile
            35                  40                  45

Gly Glu Ile Tyr Pro Gly Ser Gly Ser Ala Tyr Tyr Asn Glu Lys Phe
        50                  55                  60

Lys Gly Lys Ala Ile Leu Thr Ala Asp Lys Ser Ser Ser Thr Ala Tyr
65                  70                  75                  80

Met Glu Phe Ser Ser Leu Thr Ser Glu Asp Ser Ala Val Phe Phe Cys

```
                      85                  90                  95
Ala Arg Arg Gly Asp Gly Ser Leu Gly Phe Ala His Trp Gly Gln Gly
                100                 105                 110

Thr Leu Val Thr Val Ala Ala
        115

<210> SEQ ID NO 12
<211> LENGTH: 117
<212> TYPE: PRT
<213> ORGANISM: Mus musculus

<400> SEQUENCE: 12

Gln Val Gln Leu Gln Gln Ser Gly Ala Glu Leu Val Lys Pro Gly Ala
  1               5                  10                  15

Ser Val Lys Ile Ser Cys Lys Ala Thr Gly Tyr Thr Phe Ser Ser Tyr
                 20                  25                  30

Trp Ile Glu Trp Met Lys Gln Arg Pro Gly His Gly Leu Glu Trp Ile
             35                  40                  45

Gly Asp Phe Leu Pro Gly Ser Gly Ser Tyr Phe Asn Glu Lys Phe
         50                  55                  60

Lys Gly Arg Ala Thr Phe Thr Ala Asp Ser Ser Asn Thr Ala Phe
 65                  70                  75                  80

Met Glu Phe Gly Ser Leu Thr Ser Glu Asp Ser Ala Val Tyr Tyr Cys
                 85                  90                  95

Ala Arg Arg Gly Ala Gly Arg Val Asp Tyr Trp Gly Gln Gly Thr Thr
                100                 105                 110

Leu Thr Val Ser Ala
        115

<210> SEQ ID NO 13
<211> LENGTH: 123
<212> TYPE: PRT
<213> ORGANISM: Mus musculus

<400> SEQUENCE: 13

Glu Val Gln Gly Val Glu Ser Gly Gly Gly Leu Val Lys Pro Gly Gly
  1               5                  10                  15

Ser Leu Lys Leu Ser Cys Ala Ala Ser Gly Phe Thr Phe Ser Asp Tyr
                 20                  25                  30

Tyr Met Tyr Trp Val Arg Gln Thr Pro Glu Lys Arg Leu Glu Trp Val
             35                  40                  45

Ala Thr Ile Ser Asp Gly Gly Ser Tyr Thr Tyr Tyr Pro Asp Ser Val
         50                  55                  60

Lys Gly Arg Phe Thr Ile Ser Arg Asp Asn Ala Lys Asn Asn Leu Tyr
 65                  70                  75                  80

Leu Gln Met Ser Ser Leu Lys Ser Glu Asp Thr Ala Met Tyr Tyr Cys
                 85                  90                  95

Ala Arg Asp Lys Ala Tyr Tyr Gly Asn Tyr Gly Asp Ala Met Asp Tyr
                100                 105                 110

Trp Gly Gln Gly Thr Ser Val Thr Val Ser Ser
        115                 120

<210> SEQ ID NO 14
<211> LENGTH: 112
<212> TYPE: PRT
<213> ORGANISM: Mus musculus

<400> SEQUENCE: 14
```

-continued

```
Glu Val Gln Leu Gln Glu Ser Gly Pro Asp Leu Val Lys Pro Ser Gln
 1               5                  10                  15

Ser Leu Ser Leu Thr Cys Thr Val Thr Gly Tyr Pro Ile Thr Ser Gly
            20                  25                  30

Tyr Thr Trp His Trp Ile Arg Gln Phe Pro Cys Leu Glu Trp Met Gly
        35                  40                  45

Tyr Met His Tyr Asn Gly Ser Thr Asn Tyr Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Glu Phe
                85                  90                  95

Ser Ser Trp Asp Tyr Trp Gly Gln Gly Thr Ser Val Thr Val Ser Ala
            100                 105                 110
```